(12) United States Patent
Hackett

(10) Patent No.: US 10,285,797 B2
(45) Date of Patent: May 14, 2019

(54) PROTECTING AGAINST CEREBRAL EMBOLISM

(71) Applicant: St. Jude Medical, LLC, Abbott Park, IL (US)

(72) Inventor: Steven S. Hackett, Maple Grove, MN (US)

(73) Assignee: St. Jude Medical, LLC, Abbott Park, IL (US)

( * ) Notice: Subject to any disclaimer, the term of this patent is extended or adjusted under 35 U.S.C. 154(b) by 1474 days.

(21) Appl. No.: 13/746,712

(22) Filed: Jan. 22, 2013

(65) Prior Publication Data

US 2014/0207174 A1 Jul. 24, 2014

(51) Int. Cl.
*A61F 2/01* (2006.01)
*A61B 17/00* (2006.01)
*A61B 17/12* (2006.01)

(52) U.S. Cl.
CPC ...... *A61F 2/01* (2013.01); *A61B 2017/00358* (2013.01); *A61B 2017/00876* (2013.01); *A61B 2017/12054* (2013.01); *A61B 2017/12086* (2013.01); *A61F 2002/011* (2013.01);
(Continued)

(58) Field of Classification Search
CPC ...... A61F 2/01; A61F 2002/011; A61F 2/061; A61F 2/013; A61F 2002/015; A61F 2002/016; A61F 2002/9528; A61F 2002/9534; A61F 2230/0076; A61F 2250/0059; A61B 2017/12054; A61B 2017/00358; A61B 17/1204; A61B 17/12109; A61B 17/1214; A61B 17/12145; A61B 17/12168; A61B 17/12172
See application file for complete search history.

(56) References Cited

U.S. PATENT DOCUMENTS

| 5,649,906 A * | 7/1997 | Gory ............ A61F 2/01 604/175 |
| 6,676,694 B1 * | 1/2004 | Weiss ........... A61F 2/07 606/108 |
| 7,232,453 B2 | 6/2007 | Shimon |

(Continued)

FOREIGN PATENT DOCUMENTS

| KR | 20110040187 A | 4/2011 |
| WO | 03073961 A1 | 9/2003 |

(Continued)

OTHER PUBLICATIONS

International Search Report for Application No. PCT/US2014/012070 dated Apr. 9, 2014.
(Continued)

*Primary Examiner* — Anh T Dang
(74) *Attorney, Agent, or Firm* — Lerner, David, Littenberg, Krumholz & Mentlik, LLP

(57) ABSTRACT

A permeable plug may be temporarily deployed in a patient to protect blood vessels from blockage by various debris. The plug includes a body formed from a filtering material. The body is collapsible for delivery to a location in a blood vessel and expandable to a filtering configuration in which the body occupies a cross-section of the blood vessel and is held in place by its own expansive force. At least one stud is connected to the body for use in deployment of the plug within the blood vessel and retrieval of the plug from the blood vessel.

16 Claims, 3 Drawing Sheets

(52) U.S. Cl.
CPC ............... *A61F 2230/0076* (2013.01); *A61F 2250/0098* (2013.01)

(56) References Cited

U.S. PATENT DOCUMENTS

| | | | |
|---|---|---|---|
| 7,879,062 B2* | 2/2011 | Galdonik et al. | 606/200 |
| 8,066,757 B2* | 11/2011 | Ferrera | A61B 17/221 |
| | | | 606/159 |
| 2006/0247572 A1* | 11/2006 | McCartney | 604/19 |
| 2007/0186933 A1* | 8/2007 | Domingo et al. | 128/207.15 |
| 2007/0213685 A1 | 9/2007 | Bressler et al. | |
| 2008/0065145 A1 | 3/2008 | Carpenter | |
| 2008/0119886 A1* | 5/2008 | Greenhalgh et al. | 606/200 |
| 2008/0147111 A1* | 6/2008 | Johnson | A61F 2/01 |
| | | | 606/200 |
| 2009/0163926 A1 | 6/2009 | Sos | |
| 2009/0326575 A1 | 12/2009 | Galdonik et al. | |

FOREIGN PATENT DOCUMENTS

| | | |
|---|---|---|
| WO | 2004012587 A2 | 2/2004 |
| WO | 2007121405 | 10/2007 |
| WO | 2012166804 A1 | 12/2012 |

OTHER PUBLICATIONS

European Office Action for EP Application No. 14704948.0, dated Jun. 20, 2018.

* cited by examiner

PROTECTING AGAINST CEREBRAL EMBOLISM

BACKGROUND OF THE INVENTION

The present invention is related to protecting against embolism, and more particularly to devices, systems, and methods for filtering blood flow in the carotid arteries so as to provide cerebral embolic protection.

A frequent risk in medical procedures is the risk that the procedure will give rise to the formation of potentially life-threatening debris in the patient's bloodstream. Such debris may be in the form of plaque or thrombi, which may travel through the patient's vasculature and become lodged in a position that blocks blood flow. For example, during coronary interventions, plaque may become dislodged and/or thrombi may form, both of which could migrate to the carotid arteries via the greater vessels, possibly blocking the carotid arteries and causing a stroke.

BRIEF SUMMARY OF THE INVENTION

It has been recognized that the risk of stroke associated with medical procedures can be reduced by using a filter to protect those vessels which are at risk from the procedure.

It has also been recognized that for medical procedures which require the passage of instruments through the aortic arch, filters used to protect against stroke should not interfere with such passage.

In view of the need to protect against stroke during medical procedures which require the passage of instruments though the aortic arch, the present apparatus, system and method were conceived and developed.

In an illustrative embodiment, a permeable plug for a blood vessel is provided. The plug includes a body formed from a filtering material having a collapsed configuration and an expanded configuration, the body in the expanded configuration being sized and shaped to occupy substantially an entire cross-section of the blood vessel; and at least one stud having a first end connected to the body and a free end, the first end having a first cross-section and the free end having a second cross-section that is larger than the first cross-section.

BRIEF DESCRIPTION OF THE DRAWINGS

Various embodiments of the present system and method will now be discussed with reference to the appended drawings. It is appreciated that these drawings depict only some embodiments and are therefore not to be considered as limiting the scope of the present system and method.

DETAILED DESCRIPTION

In the description that follows, the terms "proximal" and "distal" are to be taken as relative to a user (e.g., a surgeon or an interventional cardiologist) of the disclosed devices and methods. Accordingly, "proximal" is to be understood as relatively close to the user, and "distal" is to be understood as relatively farther away from the user.

Figure 1:
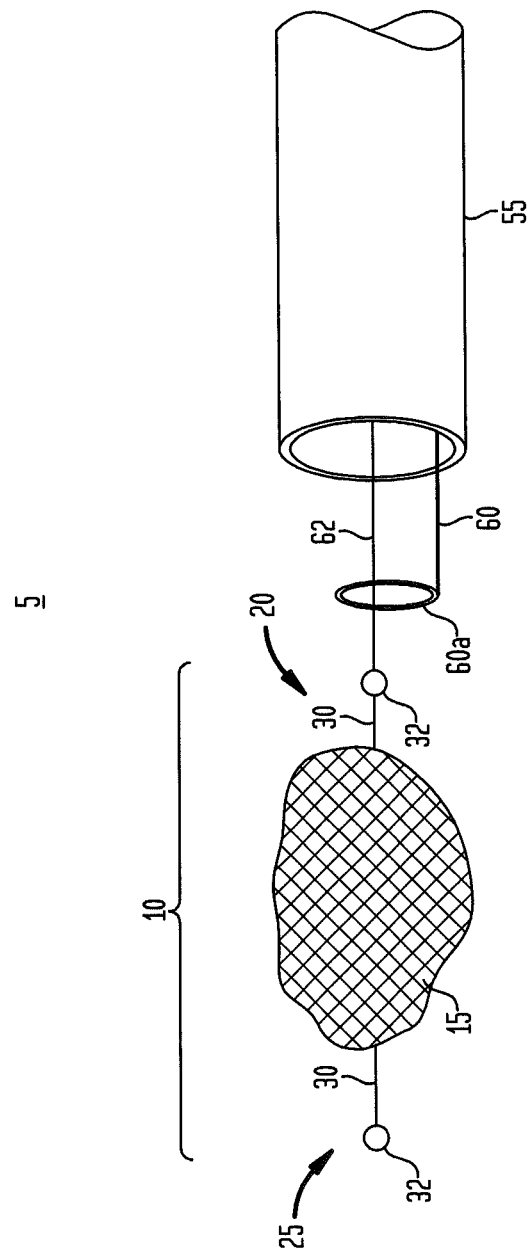
FIG. 1 is a side perspective view of a permeable blood vessel plug system in accordance with a first embodiment.

Referring to FIG. 1, there is shown a side perspective view of a permeable blood vessel plug system 5 in accordance with a first embodiment. The plug system 5 includes a permeable blood vessel plug 10 having a body 15 and two studs 20 and 25. The body 15 of plug 10 may be formed from a woven, braided, or knitted material having openings of sufficient size to allow the passage of blood, but block the passage of particulates greater than a certain size. As such, body 15 acts as a filter. Further, the material of body 15 may be treated with a conventional anti-coagulant in order to inhibit the coagulation of blood on the body and thus maintain its filtering efficiency.

The body 15 is generally hollow, but is collapsible to fit within sheath 55 for delivery and removal from a patient. In that regard, body 15 may be formed from a shape-memory material, such as a nickel titanium alloy (NiTi, or "nitinol"), that is readily collapsible and that will automatically expand to an operative shape upon deployment from the sheath 55, described below. For example body 15 may be formed from braided nitinol wire, from nitinol wire woven to form a mesh, from a simple closed nitinol surface perforated with a plurality of small apertures, or from other such structures. Alternatively, body 15 may be formed from other metals, metal alloys, or polymers, such as nylon or polyethylene, that are capable of being woven or otherwise formed into a hollow shape that is porous and that may be collapsed within sheath 55 for delivery into and removal from the patient, but that will take on an expanded shape when deployed from the sheath. Still further, body 15 may be formed with a nitinol or other shape-memory frame supporting a fabric layer formed from woven polyester, nylon, polyethylene or similar material. The shape memory frame will cause the fabric layer to achieve an expanded shape upon deployment from sheath 55.

In some embodiments, the body 15 of plug 10 may be made up of an outer layer of a woven, braided, or knitted material that surrounds a porous filler material. The filler material could be present to help ensure the capture of embolic debris that fits through the openings in the body's outer layer.

As noted above, the material forming body 15 should have openings of sufficient size to permit the passage of blood, but block the passage of particulates greater than a certain size. In this regard, the openings in body 15 are preferably between about 100 microns and about 1000 microns in their largest dimension when the body is in the expanded configuration. Thus, for example, when body 15 is made from nitinol braid, the braid spacing is approximately in the range of 100-1000 microns when the body is in the expanded configuration.

When body 15 is in the collapsed configuration, the openings would be much smaller than they are in the expanded configuration. Further, the size of the openings may vary with the degree to which the body is collapsed. Accordingly, plug 10 may be provided in several sizes so as not to be over-sized or under-sized for the blood vessel in which it will be deployed. Such sizing not only assures that the plug 10 will occupy substantially the entire cross-section of the blood vessel in which it will be deployed, but also assures that the plug will expand by an appropriate amount to provide openings that are not too small or too large.

Studs 20 and 25 are connected at spaced locations to body 15. Either one or both of studs 20 and 25 may be radiopaque so that the stud(s) may be readily located through, for example, X-ray imaging or fluoroscopy when plug 10 is positioned within a patient. The imaging of studs 20 and 25 may help a user place plug 10 in the proper position and orientation during deployment, and locate the plug for recapture and removal from the patient. In the embodiment of FIG. 1, each of studs 20 and 25 includes a rod or wire 30 having a first end connected to body 15 and a free end, and an enlarged mass 32 on the free end. Mass 32 may be solid or hollow, and may have a spherical, elliptical, rectangular or any other desired shape. Mass 32 has a larger transverse cross section than wire 30. That is, wire 30 may have a first cross-section and mass 32 may have a second cross-section that is larger than the first cross-section.

Sheath 55 may extend from a distal portion sized to hold one or more plugs 10 in a collapsed configuration for delivery into and removal from a patient, to a proximal portion that remains outside of the patient's body for manipulation by the user. Alternatively, sheath 55 may have a length that is slightly longer than the length of one or more plugs 10 in the collapsed configuration, and may be connected to another shaft member which extends outside of the patient's body so that manipulation of the shaft member by the user will result in a corresponding movement of the sheath. In either event, the sheath 55 or sheath/shaft combination may be steerable as is known in the art in order to maneuver the sheath through the patient's vasculature to the desired deployment site.

A snare 60 extends from the distal opening of sheath 55. The snare 60 may be inserted in the proximal end of sheath 55, may track through the sheath to be utilized in a blood vessel, and may be used to engage one of studs 20 and 25. That is, snare 60 may be designed to engage either one, or both, of studs 20 and 25, but in either case snare 60 may engage only one of the studs at a given time. In an embodiment like that shown in FIG. 1, snare 60 includes a loop 60a which engages one of studs 20 and 25 by being maneuvered to pass over the stud and tightened. Loop 60a may disengage from the stud by being loosened and maneuvered away from the stud.

The use of sheath 55 to deliver one or more plugs 10 to a desired location within a patient's aorta will now be described with reference to FIGS. 1-3. To begin, one or more plugs 10 are compressed to a collapsed condition and loaded into sheath 55. The sheath 55 may then be inserted into the patient and maneuvered to the patient's aortic arch using a conventional technique, such as a transfemoral approach, a left subclavian approach, a ventricular apex approach, or other known techniques. In any event, when the distal end of sheath 55 reaches a desired position within the patient's vasculature, the user employs snare 60 to deploy a plug 10 from sheath 55, and then releases the deployed plug from the snare.

The enlarged mass 32 of one or both of studs 20 and 25 may be magnetized to facilitate deployment and recapture of plug 10. For example, the mass 32 of stud 20 may be magnetized and magnetically coupled to a magnetically-tipped wire 62 extending through sheath 55. The loop 60a of snare 60 may then track over wire 62 to insure that the snare passes over and correctly retracts about stud 20 during deployment, as well as during recapture.

Figure 2A:
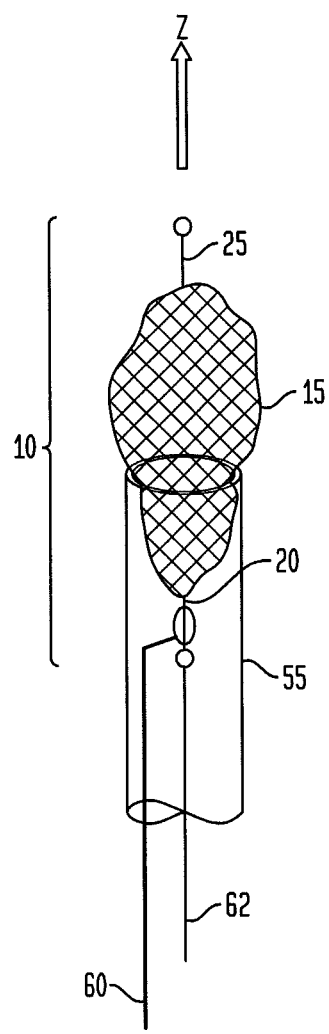
FIGS. 2A and 2B are highly schematic views depicting the deployment and recapture of the permeable blood vessel plug of FIG. 1.
Figure 2B:
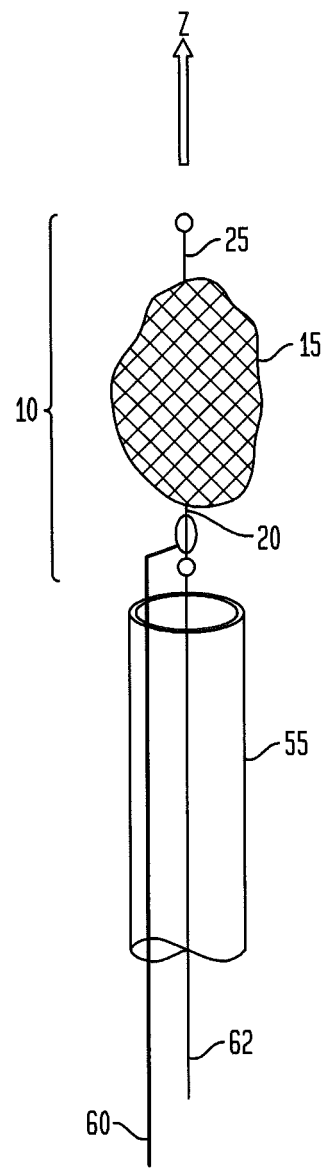

FIGS. 2A and 2B are highly schematic views depicting the deployment and recapture of permeable blood vessel plug 10 of FIG. 1. As can be seen in FIG. 2A, plug 10 is deployed by moving snare 60 and/or wire 62 distally relative to sheath 55, in the direction of arrow Z. As plug 10 emerges from sheath 55, the plug expands from its collapsed configuration and the openings of the plug enlarge. As can be seen from FIG. 2B, when plug 10 is clear of sheath 5, the plug is free to expand within the boundaries of the blood vessel in which it has been deployed. Once deployed, plug 10 may be decoupled from wire 62 by simply pulling the wire proximally. Frictional forces between plug 10 and the surrounding blood vessel will hold the plug in place as wire 62 is magnetically decoupled from stud 20. Subsequently, snare 60 may be manipulated to release loop 60a from stud 20.

When plug 10 is deployed from sheath 55, body 15 expands into a shape that conforms to the blood vessel within which it is deployed. In this manner, the body 15 fills the entire cross-section of the vessel and no blood can pass through such cross-section without passing through the body. As expanded within a blood vessel, body 15 may be hollow, wadded, or filled with a porous material. In any of these arrangements, body 15 has sufficient porosity or openings to permit blood to flow therethrough, but to trap debris. Body 15 is held in place within the blood vessel by an expansive force exerted on the blood vessel by the body material. Accordingly, the material of body 15 must have sufficient radial strength to maintain its position within the blood vessel in the presence of flowing blood. Nevertheless, the radial strength should be low enough to avoid vessel damage in the event that body 15 is dragged along the vessel during positioning or recapture of plug 10.

Once the medical procedure has been completed, plug 10 may be recaptured and removed from the patient generally by reversing the deployment procedure. That is, the distal end of sheath 55 may be positioned adjacent the stud 20 of plug 10 and, with loop 60a threaded thereover, wire 62 may be manipulated to magnetically couple to the mass 32 at the end of the stud. Snare 60 may then be advanced distally over stud 20 and loop 60a tightened. The snare 60 and wire 62 may then be pulled proximally relative to sheath 55, in the direction opposite that of arrow Z, to draw plug 10 into the open end of the sheath.

Figure 3:
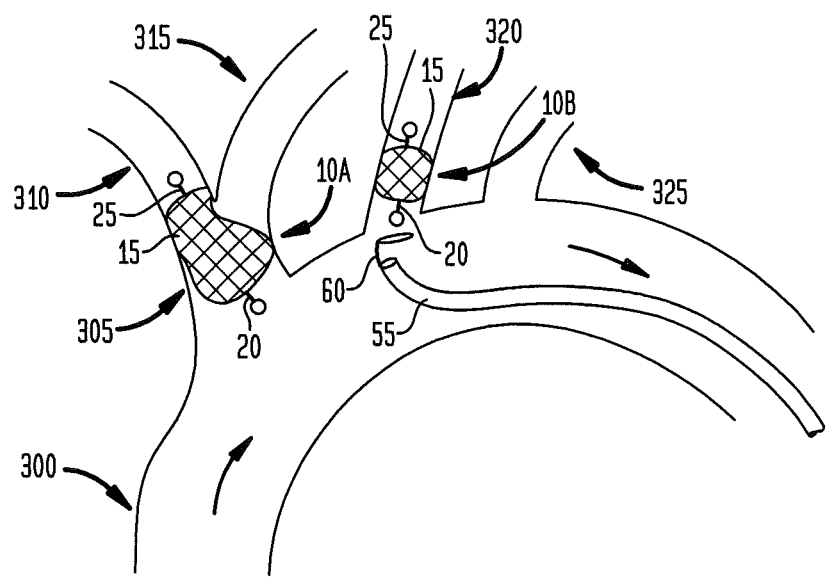
FIG. 3 is a highly schematic view showing how the permeable blood vessel plug of FIG. 1 may be used in a transcatheter aortic valve implantation (TAVI) procedure.

FIG. 3 is a highly schematic view showing the placement of two plugs 10A and 10B in a patient's vasculature in preparation for performing a transcatheter aortic valve implantation (TAVI) procedure. The figure includes representations of a patient's aortic arch 300, innominate artery 305, right subclavian artery 310, right common carotid artery 315, left common carotid artery 320, and left subclavian artery 325. A first plug 10A has been placed in the innominate artery 305 at the juncture of the right subclavian artery 310 and the right common carotid artery 315, and a second plug 10B has been placed in the left common carotid artery 320. As shown in FIG. 3, plugs 10A and 10B have been delivered through a transfemoral approach. However, either or both of plugs 10A and 10B may be delivered in a retrograde direction from the left subclavian artery 325, in an antegrade direction from the ventricular apex, or using known alternatives. Plugs 10A and 10B may have been deployed using the procedure described above for deploying plug 10.

Once plugs 10A and 10B have been properly deployed, sheath 55 and snare 60 (and optional wire 62) are removed from the patient and a medical procedure, such as a TAVI procedure, may be performed. Since the plug delivery system (sheath 55, and snare 60 and optional wire 62) has been removed from the patient and plugs 10A and 10B are positioned in the branching arteries, the TAVI delivery system may proceed through the patient's vasculature unencumbered by the plugs or plug delivery system. In particular, the aortic arch is cleared for passage of the TAVI delivery system. Nonetheless, the permeable plugs 10A and 10B are in place to filter blood flowing through the aortic arch and into the innominate artery 305 and left common carotid artery 320, thereby protecting those arteries and organs downstream thereof against blockage due to debris resulting from the TAVI procedure. It will be appreciated that one or more additional plugs may be deployed in the subclavian artery 325 or any other arteries as desired to similarly protect such arteries and the organs downstream thereof from blockage.

Upon completion of the valve implantation, plugs 10A and 10B may be removed from the patient. Plugs 10A and 10B may be removed by reintroducing sheath 55 and snare 60 (and optionally wire 62) into the patient, and maneuvering the sheath to a position adjacent one of the plugs. The snare 60 may then be manipulated by the user to grasp one of the studs 20 and 25 on the plug. Once the snare 60 has been secured to a stud, the snare may be retracted to draw the associated plug back into sheath 55.

Before drawing plugs 10A and 10B into sheath 55 for removal from the patient, the plugs may be pulled into the aortic arch 300 to dislodge filtered debris to the peripheral circulation. Optionally, debris may be aspirated from plugs 10A and 10B by applying a vacuum through sheath 55, or through some other aspiration device, prior to drawing the plugs into the sheath. In any event, as a plug enters the sheath 55, it will be compressed to the collapsed configuration, and any debris captured by the plug will be trapped in the sheath. Preferably, the upstream plug 10A is retrieved first, enabling the downstream plug 10B to remain in place to capture any material which may become dislodged and enter the bloodstream by movement of the upstream plug. After the first plug has been retrieved and drawn into sheath 55, the procedure may be repeated to retrieve any additional plugs that previously had been deployed. Where a plurality of plugs have been deployed, the plugs are preferably retrieved in order from the most upstream plug to the most downstream plug to maximize the ability to capture any debris that may be dislodged upon the retrieval of a plug.

It should be noted that FIG. 3 depicts an illustrative use of permeable blood vessel plugs 10A and 10B, and that use of the plugs is not limited to the context of FIG. 3. For example, plugs like those depicted in FIG. 3 may be used to filter blood flowing into one or more of the right common carotid artery 315, left internal carotid artery (not shown), right internal carotid artery (not shown), left external carotid artery (not shown), and right external carotid artery (not shown). Indeed, plugs like those depicted in FIG. 3 may be inserted in any one blood vessel or combination of blood vessels as desired. The plug used for any particular vessel may be selected from an available set of plugs of various sizes and shapes.

Although the system, method, and apparatus herein have been described with reference to particular embodiments, it is to be understood that these embodiments are merely illustrative of the principles and applications of the present system and method. It is therefore to be understood that numerous modifications may be made to the illustrative embodiments and that other arrangements may be devised without departing from the spirit and scope of the present system and method as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A permeable plug for a blood vessel, comprising:
a body formed from a filtering material having a collapsed configuration and an expanded configuration, the body in the expanded configuration being sized and shaped to occupy substantially an entire cross-section of the blood vessel, the filtering material comprising a layer of woven, braided, or knitted material that surrounds a porous filler material, and the body having a radial strength sufficient to maintain the body's position within the blood vessel in the presence of flowing blood when the body is in the expanded configuration in the blood vessel, yet low enough to avoid blood vessel damage in the event that the body in the expanded configuration is dragged along the blood vessel; and
at least one stud having a first end connected to the body and a free end, the first end having a first cross-section and the free end having a second cross-section that is larger than the first cross-section.

2. The plug as recited in claim 1, wherein the filtering material comprises a layer of woven material.

3. The plug as recited in claim 1, wherein the filtering material comprises a layer of braided material.

4. The plug as recited in claim 1, wherein the filtering material comprises a layer of knitted material.

5. The plug as recited in claim 1, wherein the body is treated with an anti-coagulant.

6. The plug as recited in claim 1, wherein the body comprises a shape-memory material.

7. The plug as recited in claim 6, wherein the shape-memory material is a nickel titanium alloy.

8. The plug as recited in claim 1, wherein the body has openings that are between about 100 microns and about 1000 microns in their largest dimension when the body is in the expanded configuration.

9. The plug as recited in claim 1, wherein the at least one stud is radiopaque.

10. The plug as recited in claim 1, wherein the at least one stud is magnetized.

11. A permeable blood vessel plug system, comprising:
a permeable plug having a body formed from a filtering material having a collapsed configuration and an expanded configuration, the body in the expanded configuration being sized and shaped to occupy substantially an entire cross-section of the blood vessel, the filtering material comprising a layer of woven, braided, or knitted material that surrounds a porous filler material, and the body having a radial strength sufficient to maintain the body's position within the blood vessel in the presence of flowing blood when the body is in the expanded configuration in the blood vessel, yet low enough to avoid blood vessel damage in the event that the body in the expanded configuration is dragged along the blood vessel, and at least one stud having a first end connected to the body and a free end, the first end having a first cross-section and the free end having a second cross-section that is larger than the first cross-section; and
a snare for engaging the plug during removal of the plug from the blood vessel.

12. The system as recited in claim 11, wherein the snare comprises a loop for engaging the at least one stud.

13. The system as recited in claim 11, further comprising a sheath used for at least one of deployment of the plug and recapture of the plug.

14. The system as recited in claim 11, wherein the at least one stud is magnetized, and the system further comprises a magnetically-tipped wire operable to magnetically couple with the magnetized stud.

15. The system as recited in claim 11, wherein the body has openings that are between about 100 microns and about 1000 microns in their largest dimension when the body is in the expanded configuration.

16. The system as recited in claim 11, wherein the at least one stud is radiopaque.

* * * * *